US009821299B2

(12) United States Patent
Lai et al.

(10) Patent No.: US 9,821,299 B2
(45) Date of Patent: Nov. 21, 2017

(54) PROCESS FOR PRODUCING PHOSPHORUS MODIFIED ZEOLITE CATALYSTS

(71) Applicant: ExxonMobil Research and Engineering Company, Annandale, NJ (US)

(72) Inventors: Wenyih Frank Lai, Bridgewater, NJ (US); Merci A. Hamilton, Easton, PA (US); Stephen J. McCarthy, Center Valley, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 1015 days.

(21) Appl. No.: 13/652,631

(22) Filed: Oct. 16, 2012

(65) Prior Publication Data

US 2013/0096358 A1    Apr. 18, 2013

Related U.S. Application Data

(60) Provisional application No. 61/548,015, filed on Oct. 17, 2011, provisional application No. 61/548,038, (Continued)

(51) Int. Cl.
*B01J 29/40* (2006.01)
*C07C 1/24* (2006.01)
(Continued)

(52) U.S. Cl.
CPC ............. *B01J 29/40* (2013.01); *B01J 21/04* (2013.01); *B01J 29/00* (2013.01); *B01J 29/83* (2013.01);
(Continued)

(58) Field of Classification Search
CPC ... B01J 21/04; B01J 29/00; B01J 29/40; B01J 29/83; B01J 35/0002; B01J 35/0026;
(Continued)

(56) References Cited

U.S. PATENT DOCUMENTS 3,354,078 A    11/1967 Miale et al.
3,702,886 A *  11/1972 Argauer ................. 423/705
(Continued)

FOREIGN PATENT DOCUMENTS

CN    1084431 A    3/1994
CN    1147420 A    10/1995
(Continued)

OTHER PUBLICATIONS

Balkrishnan et al., "Catalytic activity and selectivity in the conversion of methanol to light olefins", Journal of Molecular Catalysis, vol. 17, No. 2-3, Nov. 1, 1982, pp. 261-270: ISSN: 0304-5102.
(Continued)

*Primary Examiner* — Melvin C Mayes
*Assistant Examiner* — Smita Patel
(74) *Attorney, Agent, or Firm* — Liza Negron

(57) ABSTRACT

In a process for producing a phosphorus-modified zeolite catalyst, an aqueous reaction mixture comprising a source of silica and a source of an organic directing agent effective to direct the synthesis of a desired zeolite is heated at a temperature and for a time sufficient to produce crystals of the desired zeolite. Wet zeolite crystals can then be separated from the reaction mixture and, without removing all the water from the wet zeolite crystals, the zeolite can be converted into the ammonium form by ion exchange, and the crystals can be treated with a phosphorus compound. The phosphorus-treated, ammonium-exchanged zeolite can then be formed into a catalyst to be heated in one or more stages to remove the water and organic directing agent from the
(Continued)

zeolite crystals and to convert the zeolite to the hydrogen form.

15 Claims, 3 Drawing Sheets

Related U.S. Application Data filed on Oct. 17, 2011, provisional application No. 61/548,044, filed on Oct. 17, 2011, provisional application No. 61/548,052, filed on Oct. 17, 2011, provisional application No. 61/548,057, filed on Oct. 17, 2011, provisional application No. 61/548,064, filed on Oct. 17, 2011.

(51) Int. Cl.

| | | |
|---|---|---|
| B01J 29/83 | (2006.01) | |
| C01B 39/54 | (2006.01) | |
| C07C 1/22 | (2006.01) | |
| B01J 37/04 | (2006.01) | |
| B01J 37/06 | (2006.01) | |
| B01J 37/28 | (2006.01) | |
| B01J 21/04 | (2006.01) | |
| B01J 29/00 | (2006.01) | |
| B01J 35/00 | (2006.01) | |
| B01J 35/10 | (2006.01) | |
| B01J 37/00 | (2006.01) | |
| B01J 37/02 | (2006.01) | |
| C10G 3/00 | (2006.01) | |
| C07C 2/86 | (2006.01) | |
| C07C 41/09 | (2006.01) | |
| C07C 1/20 | (2006.01) | |
| B82Y 30/00 | (2011.01) | |
| B82Y 40/00 | (2011.01) | |

(52) U.S. Cl.
CPC ......... *B01J 35/002* (2013.01); *B01J 35/0026* (2013.01); *B01J 35/1004* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 35/1085* (2013.01); *B01J 37/0009* (2013.01); *B01J 37/0201* (2013.01); *B01J 37/04* (2013.01); *B01J 37/06* (2013.01); *B01J 37/28* (2013.01); *B82Y 30/00* (2013.01); *B82Y 40/00* (2013.01); *C01B 39/54* (2013.01); *C07C 1/20* (2013.01); *C07C 1/22* (2013.01); *C07C 1/24* (2013.01); *C07C 2/864* (2013.01); *C07C 41/09* (2013.01); *C10G 3/49* (2013.01); *B01J 2229/186* (2013.01); *B01J 2229/36* (2013.01); *B01J 2229/37* (2013.01); *B01J 2229/42* (2013.01); *C10G 2400/02* (2013.01); *C10G 2400/04* (2013.01); *Y02P 20/125* (2015.11); *Y02P 30/20* (2015.11)

(58) Field of Classification Search
CPC B01J 35/1004; B01J 35/1014; B01J 35/1019; B01J 35/1038; B01J 35/1042; B01J 35/1061; B01J 35/1085; B01J 37/0009; B01J 37/0201; B01J 37/04; B01J 37/06; B01J 37/28; B01J 2229/186; B01J 2229/36; B01J 2229/37; B01J 2229/42; B82Y 40/00; B82Y 30/00; C01B 39/54; C07C 1/20; C07C 1/21; C07C 1/24; C07C 2/864; C07C 41/09; C10G 3/49
See application file for complete search history.

(56) References Cited

U.S. PATENT DOCUMENTS

| | | | |
|---|---|---|---|
| 3,709,979 A | 1/1973 | Chu | |
| 3,931,349 A | 1/1976 | Kuo | |
| 3,972,832 A | 8/1976 | Butter et al. | |
| 4,044,065 A | 8/1977 | Butter et al. | |
| 4,086,287 A * | 4/1978 | Kaeding et al. | 585/466 |
| RE29,948 E | 3/1979 | Dwyer et al. | |
| 4,536,485 A | 8/1985 | Topp-Jorgensen | |
| 4,579,994 A | 4/1986 | Kiyozumi et al. | |
| 4,590,321 A | 5/1986 | Chu | |
| 4,665,251 A | 5/1987 | Chu | |
| 5,110,776 A * | 5/1992 | Chitnis et al. | 502/64 |
| 5,171,921 A | 12/1992 | Gaffney et al. | |
| 5,427,753 A | 6/1995 | Miura et al. | |
| 5,573,990 A | 11/1996 | Wang et al. | |
| 5,658,454 A | 8/1997 | Absil et al. | |
| 5,772,980 A * | 6/1998 | Sul et al. | 423/705 |
| 6,417,421 B1 | 7/2002 | Yao | |
| 6,423,879 B1 | 7/2002 | Brown et al. | |
| 6,504,072 B1 | 1/2003 | Brown et al. | |
| 6,835,863 B2 | 12/2004 | Chester et al. | |
| 7,285,511 B2 | 10/2007 | Ghosh et al. | |
| 7,304,194 B2 | 12/2007 | Ghosh et al. | |
| 7,368,410 B2 | 5/2008 | Ghosh et al. | |
| 7,399,727 B2 | 7/2008 | Ghosh et al. | |
| 7,507,685 B2 | 3/2009 | Ghosh et al. | |
| 7,662,737 B2 | 2/2010 | Ghosh et al. | |
| 2005/0209492 A1 | 9/2005 | Ghosh et al. | |
| 2006/0058562 A1 | 3/2006 | Choi et al. | |
| 2007/0032690 A1 | 2/2007 | Ghosh et al. | |
| 2007/0173399 A1 | 7/2007 | Lau et al. | |
| 2007/0275852 A1 | 11/2007 | Luo et al. | |
| 2008/0146826 A1 | 6/2008 | Kaminsky et al. | |
| 2008/0275280 A1 | 11/2008 | Ghosh et al. | |
| 2008/0305945 A1 | 12/2008 | Ghosh et al. | |
| 2009/0036723 A1 | 2/2009 | Ghosh et al. | |
| 2009/0288990 A1 | 11/2009 | Xie et al. | |
| 2009/0325786 A1 | 12/2009 | Liu et al. | |
| 2010/0113850 A1 | 5/2010 | Ghosh et al. | |
| 2010/0168489 A1 | 7/2010 | Ghosh et al. | |
| 2010/0197986 A1 | 8/2010 | Midorikawa et al. | |
| 2010/0292417 A1 | 11/2010 | Nesterenko et al. | |
| 2012/0184791 A1 | 7/2012 | Chewter et al. | |

FOREIGN PATENT DOCUMENTS

| | | |
|---|---|---|
| CN | 1147420 A | 4/1997 |
| CN | 1302228 A | 7/2001 |
| CN | 102049293 A | 5/2011 |
| EP | 205300 B1 | 3/1991 |
| EP | 2036873 A | 3/2009 |
| EP | 2036873 A1 | 3/2009 |
| EP | 2082801 A1 | 7/2009 |
| WO | WO0137994 A2 | 5/2001 |

OTHER PUBLICATIONS

Zhao et al., "Effect of phosphorus on HZSM-5 catalyst for C4-olefin cracking reactions to produce propylene", Journal of Catalysis, Academic Press, Duluth, MN, US, vol. 248, No. 1, Apr. 23, 2007, pp. 29-37, ISSN: 0021-9517.

Abubakar et al., "Structural and Mechanistic Investigation of a Phosphate-Modified HZSM-5 Catalyst for Methanol Conversion",. Langmuir, vol. 22, No. 10, May 1, 2006, pp. 4846-4852, ISSN: 0743-7463.

Lee et al., "Influence of Catalytic Performance of HZSM-5 Zeolites for Methanol-to-Propylene (MTP) Process: Single and Binary Binder System", Topics in Catalysis, Kluwer Academic Publishers—Plenum Publishers, NE, vol. 53, No. 3-4, Dec. 1, 2009, pp. 247-253; ISSN: 1572-9028.

Suzuki et al., "Effect of modification of ZSM-5 type zeolite with calcium phosphate on its physico-chemical and catalytic properties", Applied Catalysis, vol. 39, May 1, 1968, pp. 315-324; ISSN: 0166-9834.

(56) References Cited

OTHER PUBLICATIONS

Ikai et al., "HZSM-5 pelletized and modified with [alpha]-Ca3(P04)2 and HP042- as a catalyst for methanol conversion", Applied Catalysis, vol. 49, No. 1, Apr. 1, 1989, pp. 143-163; ISSN: 0166-9834.

Freiding et al., "Novel extruded fixed-bed MTO catalysts with high olefin selectivity and high resistance against coke deactivation", Applied Catalysis A: General, Elsevier Science, vol. 391, No. 1, May 24, 2010, pp. 254-260; ISSN: 0926-860X.

Lee et al., "Novel aluminophosphate (A1P0) bound ZSM-5 extrudates with improved catalytic properties for methanol to propylene (MTP) reaction", Applied Catalysis A: General, Elsevier Science, vol. 374, No. 1-2, Feb. 1, 2010; ISSN: 0926-860X.

Xue et al., "Impact of Forming and Modification with Phosphoric Acid on the Acid Sites of HZSM-5", Journal of Physical Chemistry C, vol. 114, No. 37, Sep. 23, 2010; ISSN: 1932-7447.

Zhao et al., "Direct synthesis of propylene and light olefins from dimethyl ether catalyzed by modified H-ZSM-5", Catalysis Communications, Elsevier Science, vol. 7, No. 9, Sep. 1, 2006, pp. 647-650; ISSN: 1566-7367.

H. Knözinger, "H Bonding of Substituted Pyridines on Silica", Surface Sci., 41 (1974), 339.

H. Knözinger, "Specific Poisoning and Characterization of Catalytically Active Oxide Surfaces", Adv. Catal., 25 (1976), 184.; ISBN: 0-12-007825-2.

C. Morterra et al., "A case study: surface chemistry and surface structure of catalytic aluminas, as studied by vibrational spectroscopy of adsorbed species", Catalysis Today 27 (1996) 497. ISSN: 0920-5861.

G. Busca et al., "FT-IR Study of the Surface Properties of the Spinels NiAl2O4 and CoAl2O4 in Relation to Those of Transitional Aluminas", J. Catal. 131 (1991) 167.; ISSN: 0021-9517.

H. Knözinger et al., "Die Dehydrastisierung von Alkoholen an Al2O3, XIII, Einfluß der Vergiftung durch Pyridin auf Adsorption und Dehydratisierung von Alkoholen", Bunsengesellschaft Phys. Chem., 74 (1970) 1056.; ISSN: 0005-9021.

J. March: "Advanced Organic Chemistry", 3rd edition, John Wiley & Sons, (1985), p. 600; ISBN: 0-471-88841-9.

Unpublished Related U.S. Appl. No. 13/652,660.
Unpublished Related U.S. Appl. No. 13/652,669.
Unpublished Related U.S. Appl. No. 13/652,681.
Unpublished Related U.S. Appl. No. 13/652,692.
Unpublished Related U.S. Appl. No. 13/652,734.

International Search Report with Written Opinion for PCT/US2012/060393 dated Mar. 7, 2013.

International Search Report with Written Opinion for PCT/US2012/060385 dated Feb. 27, 2013. (Related Case).

International Search Report with Written Opinion for PCT/US2012/0603967 dated Mar. 6, 2013. (Related Case).

International Search Report with Written Opinion for PCT/US2012/060369 dated Feb. 27, 2013. (Related Case).

International Search Report with Written Opinion for PCT/US2012/060381 dated Feb. 27, 2013. (Related Case).

D. Mao et al., Effects of Crystal Size and Phosphorous Modification of ZSM-5 Zeolite on Its Catalytic Performance in the Conversion of Methanol to Propylene, ACTA Petrolei Sinica, vol. 25, No. 4, pp. 503-508, 2009.

A.B.M. Saad et al., Comparative study of the effects of sodium impurity and amorphisation on the Lewis acidity of gamma alumina, Applied Catalysis A: General, vol. 94, No. 1, 1993, pp. 71-83.

* cited by examiner

PROCESS FOR PRODUCING PHOSPHORUS MODIFIED ZEOLITE CATALYSTS

CROSS-REFERENCE TO RELATED APPLICATIONS

This application claims the benefit of U.S. Provisional Application No. 61/548,015, filed on Oct. 17, 2011, the entire contents of which are hereby incorporated by reference herein.

This application also claims the benefit of related U.S. Provisional Application Nos. 61/548,038, 61/548,044, 61/548,052, 61/548,057, and 61/548,064, each filed on Oct. 17, 2011, the entire contents of each of which are hereby also incorporated by reference herein. This application is also related to five other co-pending U.S. utility applications, each filed on even date herewith and claiming the benefit to the aforementioned provisional patent applications, and which are entitled "Process for Producing Phosphorus Modified Zeolite Catalysts", "Phosphorus Modified Zeolite Catalysts", "Phosphorus Modified Zeolite Catalysts", "Phosphorus Modified Zeolite Catalysts", and "Selective Dehydration of Alcohols to Dialkyl Ethers", respectively, the entire contents of each of which utility patents are hereby further incorporated by reference herein.

FIELD OF THE INVENTION

This disclosure relates to a process for producing phosphorus modified zeolite catalysts.

BACKGROUND OF THE INVENTION

Phosphorus modification is a known method of improving the performance of zeolite catalysts for a variety of chemical processes including, for example, the conversion of methanol to hydrocarbons and the methylation of toluene to produce xylenes. For example, U.S. Pat. Nos. 4,590,321 and 4,665,251 disclose a process for producing aromatic hydrocarbons by contacting one or more non-aromatic compounds, such as propane, propylene, or methanol, with a catalyst containing a zeolite, such as ZSM-5. The zeolite is modified with phosphorus oxide by impregnating the zeolite with a source of phosphate ions, such as an aqueous solution of an ammonium phosphate, followed by calcination.

In addition, U.S. Pat. No. 7,662,737 discloses a process for producing a bound phosphorus-modified zeolite catalyst, in which a zeolite, such as ZSM-5, which may be in the $NH_4^+$ or the $H^+$ form, is slurried with an aqueous solution of a phosphorus compound and then water is removed from the slurry to form a phosphorus-modified zeolite. The phosphorus-modified, pre-calcined zeolite is then mixed with an acid-treated inorganic oxide binder material and, after optional extrusion, the zeolite-binder mixture is heated at a temperature of about 400° C. or higher to form a bound zeolite catalyst. The catalyst is particularly intended for use in the alkylation of toluene with methanol to produce xylenes, but is also said to be useful in MTG processes.

Similar processes of producing phosphorus-modified toluene methylation catalysts are disclosed in U.S. Pat. Nos. 7,285,511, 7,304,194, 7,368,410, 7,399,727, and 7,507,685, and in U.S. Patent Application Publication Nos. 2008/0275280 and 2009/0036723.

U.S. Pat. No. 6,504,072 discloses selective production of para-xylene by the reaction of toluene with methanol over a severely steamed ZSM-5 catalyst combined with oxide modifier, preferably an oxide of phosphorus, to control reduction of the micropore volume of the material during the steaming step. Incorporation of phosphorus in the catalyst is conveniently accomplished by contacting the ZSM-5, either alone or in combination with a binder or matrix material, with a solution of an appropriate phosphorus compound, followed by drying and calcining to convert the phosphorus to an oxide form.

However, existing methods of phosphorus modification of zeolite catalysts tend to add significantly to the complexity and hence the cost of the catalyst production process. There is therefore significant interest in the development of a higher throughput and lower cost manufacturing procedure for making phosphorus-modified zeolite catalysts.

According to the present invention, a more efficient, lower cost process for producing a phosphorus modified zeolite catalyst is proposed in which, after separation of the as-synthesized zeolite crystals from the mother liquor, but before substantial drying, the crystals can be subjected to $NH_4^+$ ion-exchange and phosphorus treatment. The resultant $NH_4^+$-exchanged, phosphorus treated zeolite crystals can then be formed into the required shape and calcined, e.g., to remove the organic directing agent and convert the zeolite from the $NH_4^+$ form to $H^+$ form.

SUMMARY OF THE INVENTION

In one aspect, the invention can reside in a process for producing a phosphorus-modified zeolite catalyst, said process comprising: (a) heating an aqueous reaction mixture comprising a source of silica and a source of an organic directing agent effective to direct the synthesis of a desired zeolite from said mixture, said heating being conducted at a temperature and for a time sufficient to produce crystals of the desired zeolite; (b) separating wet zeolite crystals from the mixture produced in (a); (c) without removing all the water from the wet zeolite crystals, effecting the steps of (i) converting the zeolite into the ammonium form by ion exchange, and (ii) treating the crystals with a phosphorus compound; (d) forming the phosphorus-treated, ammonium-exchanged zeolite from (c) into a catalyst; and (e) heating the catalyst in one or more stages to remove the water and organic directing agent from the zeolite crystals and to convert the ammonium form zeolite to the hydrogen form.

Conveniently, the reaction mixture can also comprise a source of alumina, typically such that the molar ratio of silica to alumina in the reaction mixture can be from about 20 to about 500, e.g., from about 20 to about 150.

In one embodiment, the zeolite is ZSM-5, and/or the organic directing agent comprises n-propylamine.

Conveniently, the heating in (a) can be conducted at a temperature in the range from about 100° C. to about 200° C. for a time from about 12 hours to about 120 hours.

In additional or alternate embodiments, the separating (b) can be effected by filtration.

Conveniently, the wet zeolite crystals employed in (c) can have an Adsorption Factor from about 0.1 to less than 1.5, e.g., from about 0.2 to about 0.8.

In additional or alternate embodiments, the converting (c)(i) and the treating (c)(ii) can be effected simultaneously. Conveniently, treating (c)(ii) can be effected by impregnation, especially with the ammonium salt of a phosphorus oxyacid.

Conveniently, the forming (d) can comprise mixing the phosphorus-treated, ammonium-exchanged zeolite with a binder to form an extrudable composition, which can then be extruded to form the catalyst.

Conveniently, the heating to remove the organic directing agent from the zeolite crystals and to convert the zeolite to the hydrogen form can be effected in a single heating step. Typically, the single heating step can be conducted at a temperature from about 500° C. to about 600° C. for a time of about 2 hours to about 12 hours.

In further aspects, the invention can reside in a phosphorus-modified zeolite catalyst produced by the process described herein and/or in use of the catalyst in organic conversion reactions, especially in a process for conversion of methanol to hydrocarbons.

DETAILED DESCRIPTION OF THE EMBODIMENTS

Figure 1A:
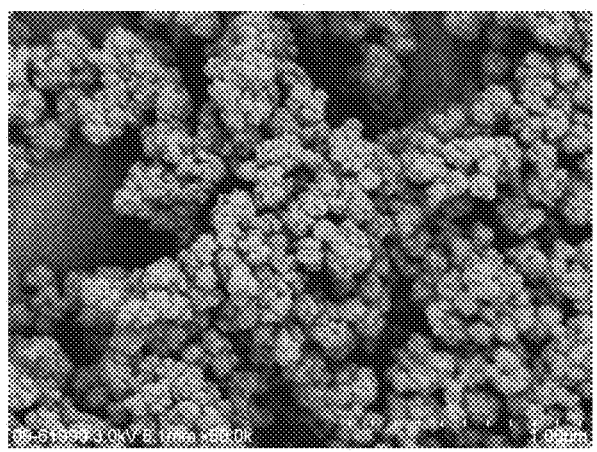
FIG. 1A shows a scanning electron microscopy (SEM) micrograph of the ZSM-5 crystals of Example 1A.

Described herein is a process for producing a phosphorus-modified zeolite catalyst. In the present process, the zeolite can be synthesized in the presence of an organic directing agent, and a phosphorus component can be added to the as-synthesized zeolite crystals prior to removal of all the water present in the crystals from the aqueous reaction mixture used to synthesize the crystals. After ion exchange to convert the zeolite crystals into the ammonium form, which can be conducted simultaneously with the phosphorus addition, the phosphorus-treated, ammonium-exchanged zeolite can be heated to remove water and organic directing agent from the zeolite crystals and to convert the zeolite to the hydrogen form.

By treating the zeolite crystals with phosphorus directly after synthesis and prior to any calcination of the zeolite, the present process can advantageously eliminate one or even two calcinations steps required in prior art processes for producing phosphorus-modified zeolite catalysts. Additionally or alternately, by allowing the phosphorus treatment to be conducted simultaneously with the ammonium exchange, the present process can obviate the need for these steps to be conducted separately. As a result, the present process can provide significant simplification and debottlenecking of production of phosphorus-modified zeolite catalysts, thereby increasing production rates and/or decreasing production costs.

In one preferred embodiment, the zeolite can comprise or be ZSM-5, and hence the remainder of the description of the present process herein focuses on the production of phosphorus-modified ZSM-5. It will, however, be appreciated that the present process can readily be modified to produce phosphorus-modified forms of other known and/or conventional zeolites.

ZSM-5 Synthesis

To produce ZSM-5 in the present process, an aqueous reaction mixture can initially be prepared to comprise a source of silica, a source of an organic directing agent effective to direct the synthesis of ZSM-5, optionally a source of alumina, and generally a source of an alkali and/or alkaline earth metal compound M. In embodiments where the optional source of alumina is present, the reaction mixture can have the following molar compositional ratios, where R designates the organic directing agent:

| Molar Ratio | Broad | Exemplary |
|---|---|---|
| OH—/SiO$_3$ | 0.05-0.5 | 0.1-0.3 |
| R/SiO$_2$ | 0.05-1.00 | 0.10-0.30 |
| H$_2$O/SiO$_2$ | 5-50 | 8-15 |
| SiO$_2$/Al$_2$O$_3$ | 20-500 | 20-150 |
| M/SiO$_2$ | 0.05-0.5 | 0.1-0.3 |

Suitable sources of silica that can be used to produce the reaction mixture described above can include, but are not necessarily limited to, colloidal silica, precipitated silica, potassium silicate, sodium silicate, fumed silica, and the like, as well as combinations thereof. Similarly, suitable sources of alumina, when present, can include, but are not limited to, hydrated aluminum oxides (such as boehmite, gibbsite, and/or pseudoboehmite), sodium aluminate, oxygen-containing aluminum salts (such as aluminum nitrate), and the like, as well as combinations thereof. Suitable sources of alkali and/or alkaline earth metal can include, but are not limited to calcium oxide, calcium hydroxide, magnesium hydroxide, magnesia, sodium hydroxide, and/or potassium hydroxide, particularly sodium and/or potassium hydroxide.

Any organic compound known to direct the synthesis of the selected zeolite can be used as the organic directing agent, R, which can include in the case of ZSM-5, tetrapropylammonium compounds, dimethylethylpropylammonium compounds, 1,2-diaminocyclohexane, ethanoltripropylammonium compounds, alkyldiamines, 1,6-hexanediol, poly(ethylene glycol), triethylene-tetramine, and the like, as well as combinations thereof. However, in one practical embodiment, the organic directing agent can comprise, consist essentially of, or be a primary monoalkylamine having 2 to 9 carbon atoms in the alkyl portion, particularly n-propylamine (n-PA), since this material favors the production of relatively small crystal (e.g., 0.05 microns or less) at relatively low crystallization temperature and relatively short crystallization times. Further details of the synthesis of ZSM-5 in the presence of primary monoalkylamines can be found, for example, in U.S. Pat. No. 4,151,189, the entire contents of which are incorporated herein by reference. It is believed that smaller directing agents, such as n-PA, which are hypothesized to not fully block the pores of the ZSM-5, can be preferred in some embodiments of the present process in facilitating ion-exchange (replacement of alkali ions such as Na$^+$ with NH$_4^+$) inside the zeolite pores, before calcination to remove the directing agent.

In some embodiments, the reaction mixture can also contains seeds, typically ZSM-5 seeds, in amount sufficient to provide at least 500 wppm, for example at least 1000 wppm or at least 10000 wppm seeds, with respect to the overall reaction mixture.

Crystallization can be carried out under either stirred or static conditions, preferably stirred conditions, at a temperature from about 100° C. to about 200° C., such as from about 110° C. to about 150° C., for a time from about 12 hours to about 120 hours, such as from about 24 hours to about 72 hours. After crystallization is relatively complete, the resultant ZSM-5 crystals can be separated from the mother liquor, generally by filtering or centrifuging, and recovered. The use of n-propylamine as the structure directing agent can generally allow the crystallization time to be reduced and can advantageously produce ZSM-5 in the form of aggregates of small crystals having an average crystal size of about 0.05 microns or less.

ZSM-5 Crystal Treatment

The ZSM-5 crystals recovered by filtering or centrifuging the mother liquor remaining after the crystallization step can usually exist in the form of a wet cake, with the ZSM-5 being mainly in the alkali (sodium) form from the presence of alkali (sodium) ions in the synthesis mixture. The wet cake can then be washed with water and, depending on its residual water level, may be partially, but typically not completely, dried by heating the wet cake, e.g., at a temperature from about 25° C. to about 120° C. for about 2 hours to about 24 hours. Partial drying can thus be conducted, e.g., until the wet cake has an Adsorption Factor from about 0.1 to less than 1.5, such as from about 0.2 to about 0.8. In this respect, the term "Adsorption Factor" is a measure of the amount of water that can be absorbed by the wet cake until the wet cake is fully saturated. In particular, the Adsorption Factor can be expressed by the following equation:

$$\text{Adsorption Factor} = \frac{\text{cc of water absorbed by wet cake for full saturation}}{\text{weight in grams of wet cake}}$$

After partial drying, the wet cake can be ion exchanged with an ammonium salt solution, so as to convert the ZSM-5 from the alkali (sodium) form to the ammonium form. In addition, before, after, or simultaneously with the ammonium exchange, the wet cake can be treated with a phosphorus compound. Phosphorus treatment can be effected by impregnating and/or spraying the wet cake with a solution of a phosphorus compound, including, but not limited to, phosphonic, phosphinous, phosphorus, and/or phosphoric acids, salts, and esters of such acids, as well as phosphorus halides, and combinations thereof. In certain preferred embodiments, in which the ammonium exchange and phosphorus impregnation are conducted simultaneously, the wet cake can be impregnated with an ammonium salt of a phosphorus oxyacid, such as ammonium monohydrogen phosphate, ammonium dihydrogen phosphate, triammonium phosphate, ammonium hypophosphate, ammonium orthophosphate, ammonium dihydrogen orthophosphate, ammonium monohydrogen orthophosphate, ammonium hypophosphite, ammonium dihydrogen orthophosphate, or the like, or some mixture thereof.

After phosphorus treatment, ZSM-5 crystals can typically contain phosphorus (P) in an amount from about 0.001 to about 0.2 grams P per gram of zeolite (about 0.1 wt % to about 20 wt. %), for example from about 0.005 to about 0.1 grams P per gram of zeolite (about 0.5 wt % to about 10 wt %) or from about 0.005 to about 0.05 grants P per gram of zeolite (about 0.5 wt % to about 5 wt %).

It will be appreciated from the foregoing discussion that, in the present process, the ZSM-5 crystals can undergo both ammonium exchange and phosphorus treatment, before the crystals can be subjected to any calcination, e.g., heating at or above 500° C.

After ammonium exchange and phosphorus treatment, the ZSM-5 crystals can be formed into a catalyst, normally by extrusion, whether with or without a separate matrix and/or binder. Suitable matrix materials can include, but are not limited to, active and inactive materials and synthetic and/or naturally occurring zeolites, as well as inorganic materials such as clays, silica, and/or metal oxides, e.g., alumina, titanic, and/or zirconia. The latter may be naturally occurring and/or in the form of gelatinous precipitates, sols, and/or gels, including mixtures of silica and metal oxides. Use of an active matrix material may enhance the conversion and/or selectivity of the catalyst in certain organic conversion processes. Inactive materials can suitably serve as diluents to control the amount of conversion in a given process, so that products can be obtained economically and orderly without employing other means for controlling the rate or reaction. Frequently, crystalline catalytic materials have been incorporated into naturally occurring clays, e.g., bentonite and kaolin. These materials (i.e., clays, oxides, etc.) can function, in part, as binders for the catalyst to improve its crush strength. Generally, the bound catalyst can include from about 1 wt % to about 100 wt % (self-bound catalyst), and usually from about 15 wt % to about 80 wt % of the active ZSM-5 material.

After forming into a catalyst, the catalyst can be heated at a temperature from about 25° C. to about 120° C. to remove residual water and then can be calcined at a temperature from about 500° C. to about 600° C. to remove the organic directing agent from the ZSM-5 crystals and/or to convert the ZSM-5 from the ammonium form to the hydrogen form. The drying and calcining can be accomplished in separate stages/steps or in a single continuous heating operation.

Uses of the Phosphorus-Modified ZSM-5 Catalyst

The phosphorus-modified ZSM-5 catalyst produced by the present process can be particularly useful in any organic conversion process where the hydrothermal stability of the catalyst is important. Examples of such processes can include, but are not necessarily limited to, fluid catalytic cracking of heavy hydrocarbons to gasoline and diesel boiling range hydrocarbons, methylation and disproportionation of toluene to produce xylem's, n-paraffin (e.g., $C_6$ and higher) cyclization, conversion of methanol to gasoline and diesel boiling range hydrocarbons, and the like, and combinations and/or integrations thereof.

ADDITIONAL OR ALTERNATE EMBODIMENTS

The invention can additionally or alternately include one or more of the following embodiments.

Embodiment 1

A process for producing a phosphorus-modified zeolite catalyst, said process comprising: (a) heating an aqueous reaction mixture comprising a source of silica and a source of an organic directing agent effective to direct the synthesis of a desired zeolite from said mixture, said healing being conducted at a temperature and for a time sufficient to produce crystals of the desired zeolite; (b) separating wet zeolite crystals from the mixture produced in (a); (c) without removing all the water from the wet zeolite crystals, effecting the steps of (i) converting the zeolite into the ammonium form by ion exchange, and (ii) treating the crystals with a phosphorus compound; (d) forming the phosphorus-treated, ammonium-exchanged zeolite from (c) into a catalyst; and (c) heating the catalyst in one or more stages to remove the water and organic directing agent from the zeolite crystals and to convert the ammonium form zeolite to the hydrogen form.

Embodiment 2

The process of embodiment 1, wherein said reaction mixture also comprises a source of alumina.

Embodiment 3

The process of embodiment 2, wherein a molar ratio of silica to alumina in the reaction mixture is from about 20 to about 500, e.g., from about 20 to about 150.

Embodiment 4

The process of any one of the previous embodiments, wherein the zeolite crystals have an average crystal size of about 0.05 microns or less.

Embodiment 5

The process of any one of the previous embodiments, wherein the zeolite comprises ZSM-5 and/or wherein said organic directing agent comprises n-propylamine.

Embodiment 6

The process of any one of the previous embodiments, wherein said temperature is from about 100° C. to about 200° C. and said time is from about 12 hours to about 120 hours.

Embodiment 7

The process of any one of the previous embodiments, wherein the separating (b) is accomplished by filtration.

Embodiment 8

The process of any one of the previous embodiments, wherein said wet zeolite crystals employed in (c) have an Adsorption Factor from about 0.1 to less than 1.5, e.g., from about 0.2 to about 0.8.

Embodiment 9

The process of any one of the previous embodiments, wherein the converting (c) (i) and the treating (c) (ii) are accomplished simultaneously.

Embodiment 10

The process of any one of the previous embodiments, wherein the treating (c) (ii) is accomplished by impregnation, e.g., by impregnating the zeolite crystals with an aqueous solution of an ammonium salt of a phosphorus oxyacid.

Embodiment 11

The process of any one of the previous embodiments, wherein the forming (d) comprises mixing the phosphorus-treated, ammonium-exchanged zeolite with a binder to form an extrudable composition and then extruding said composition to form the catalyst.

Embodiment 12

The process of any one of the previous embodiments, wherein the heating to remove the organic directing agent from the zeolite crystals and to convert the zeolite to the hydrogen form is accomplished in a single heating step, e.g., at a temperature from about 500° C. to about 600° C. for a time from about 2 hours to about 12 hours.

Embodiment 13

A phosphorus-modified zeolite catalyst produced by the process of any one of the previous embodiments.

Embodiment 14

A process for organic compound conversion employing contacting a feedstock with the phosphorus-modified zeolite catalyst of embodiment 13 under organic compound conversion conditions.

Embodiment 15

The process of embodiment 14, wherein said organic compound conversion comprises the conversion of methanol to hydrocarbons boiling in the gasoline boiling range.

The invention will now be more particularly described with reference to the following non-limiting Examples and the accompanying drawings.

EXAMPLES

In the Examples, alpha values are used to provide an indication of the catalytic cracking activity of a catalyst, compared to a standard catalyst, and to help assess the relative rate constant (rate of normal hexane conversion per volume of catalyst per unit time). The alpha value is based on the activity of a silica-alumina cracking catalyst taken as an alpha of 1 (Rate Constant≈0.016 sec$^{-1}$). The Alpha Test is described in U.S. Pat. No. 3,354,078; in the Journal of Catalysis, 4, 527 (1965); 6, 278 (1966); and 61, 395 (1980), each incorporated herein by ref; as to that description. The experimental conditions of the test used herein include a constant temperature of about 538° C. and a variable flow rate as described in detail in the Journal of Catalysis, 61, 395 (1980).

Example 1A. Preparation of Small ZSM-5 Crystals Using n-PA

A reaction mixture with about 22% solids was prepared by mixing deionized (DI) water, ~50% NaOH solution, ~45% sodium aluminate solution, n-propyl amine, Ultrasil™ silica, and about 1250 wppm ZSM-5 seed crystals. The mixture had the following molar composition ratios:

| | |
|---|---|
| $SiO_2/Al_2O_3$ | ~60 |
| $H_2O/SiO_2$ | ~11 |
| $OH/SiO_2$ | ~0.17 |
| $Na/SiO_2$ | ~0.17 |
| n-PA/Si | ~0.25 |

Figure 1C:
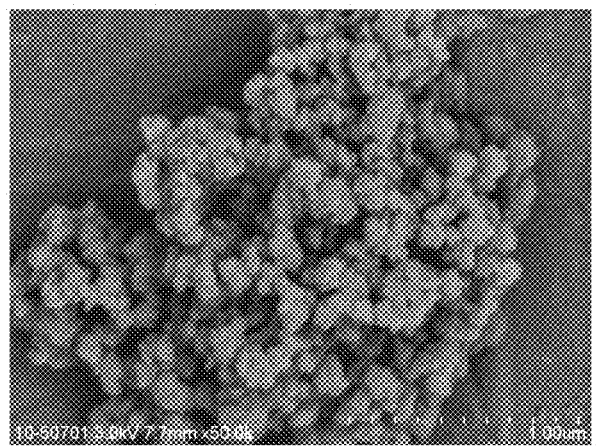
FIG. 1C shows a scanning electron microscopy (SEM) micrograph of the ZSM-5 crystals of Example 1B.
Figure 1B:
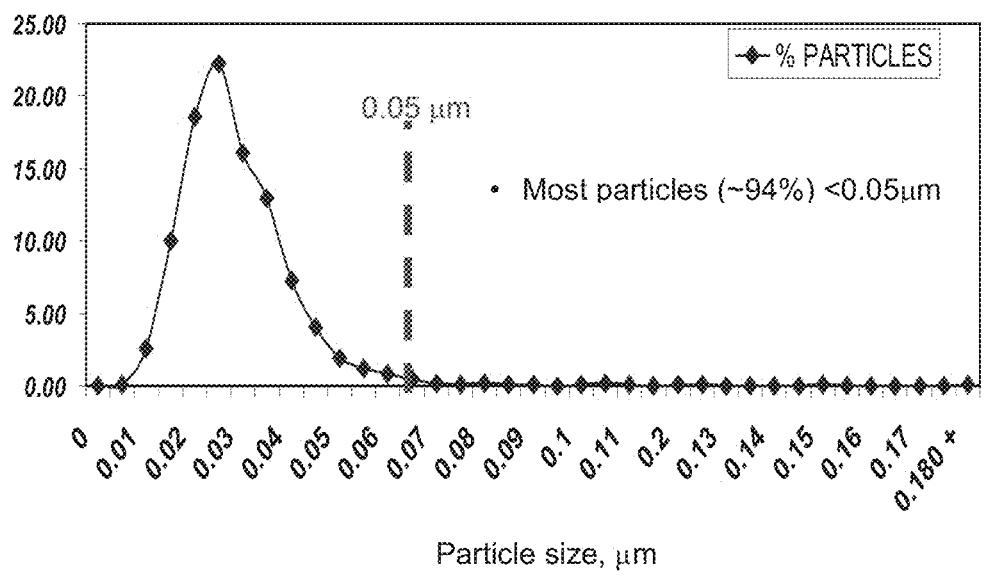
FIG. 1B shows a particle size analysis of the ZSM-5 crystals of Example 1A produced by transmission electron microscopy (TEM).

After mixing, the reaction mixture was transferred to an autoclave and reacted at about 230° F. (about 110° C.) under stirring at ~250 rpm for ~48 hours. The resulting reaction slurry was discharged and stored in a pail container. The XRD pattern of the as-synthesized material typically showed a relatively pure phase of ZSM-5 topology. The SEM of the as-synthesized material (see FIG. 1A) showed that the material was composed of agglomerates of small crystals with a size of ≤0.05 microns. The TEM particle size analysis showed that >94% of the crystals are ≤0.05 microns (see FIG. 1B). The silica to alumina molar ratio of the dried crystals was about 50. Thus, small crystal ZSM-5 can be prepared at relatively low temperature and with a reaction time of only ~48 hours.

Example 1B: Preparation of Small ZSM-5 Crystals Using n-PA

The process of Example 1A was repeated, and the XRD pattern of the as-synthesized material again typically showed a relatively pure phase of ZSM-5 topology. The SEM of the as-synthesized material (see FIG. 1C) showed that the material was composed of agglomerates of small crystals with size of ≤0.05 microns. The silica to alumina, molar ratio of the dried crystals was again ~50. The resulting slurry was flocced, decanted, washed with DI water, and then re-dispersed in a container with ammonium nitrate solution for ion-exchange. This step was repeated twice, to convert the ZSM-5 crystals to their $NH_4$ form. Air calcination of the $NH_4$ZSM-5 crystals at about 1000° F. (about 540° C.) for ~4 hours was accomplished to convert the crystals to their H-form and to yield a final product with an Alpha value of ~930 and a surface area of ~495 (~418+~77) $m^2/g$ (see Table 1 below).

Examples 2A-2C: Preparation of ZSM-5 and P-Containing ZSM-5

The process of Example 1B was repeated except that, after floccing, decanting, and washing with DI water, the resultant wet cake was divided into 3 portions. Portion No. 1 was dried at about 250° F. (about 121° C.) overnight (~8-16 hours) to make Example 2A. Portion No. 2 with an Adsorption Factor of ~0.24 was mixed with approximately 34 grams of ammonium phosphate and ~465 grams of DI water using a high shear mixer. The resulting paste was then dried at about 250° F. (about 121° C.) overnight to produce Example 2B. Portion No. 3 with an Adsorption Factor of ~0.24 was mixed with approximately 68 grams of ammonium phosphate and ~438 grams of DI water using a high shear mixer. The resulting paste was then dried at about 250° F. (about 121° C.) overnight to produce Example 2C. These resulting products showed about 0.75 wt % of P for Example 2B and about 1.5 wt % P for Example 2C.

Examples 3A-3C: Preparation of Steam Treated as-Synthesized Crystals

About 30 grams each of the products of Examples 2A, 2B, and 2C were steamed at the relatively high temperature of ~1000° F. (~540° C.) for about 48 hours to verify their hydrothermal stability. Properties of the resulting products are shown in Table 1 below for comparison.

Examples 4A-4C: Preparation of Steam Treated Calcined Crystals

Figure 2:
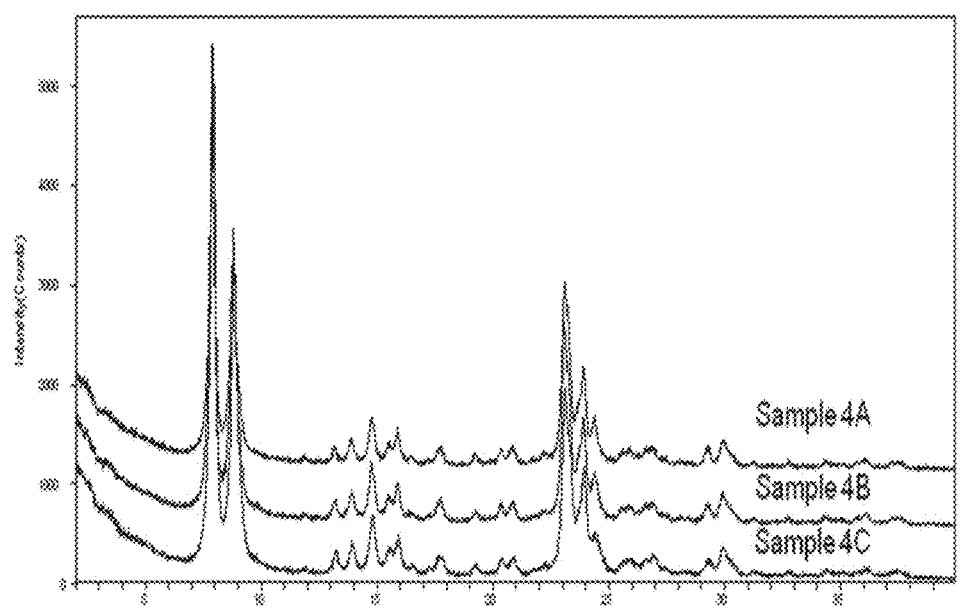
FIG. 2 shows X-ray diffraction patterns of the steamed PZSM-5 products of Examples 4A, 4B, and 4C.

About 30 grams each of the products of Examples 2A, 2B, and 2C were calcined at ~1000° F. (~540° C.) for about 4 hours in air, followed by relatively high temperature steam treatment at ~1000° F. (~540° C.) for about 48 hours, in order to verify their hydrothermal stability. XRD spectra of these three samples are shown in FIG. 2 and indicated that all steamed samples were hydrothermally stable (still crystalline in structure). Properties of the calcined steamed Examples are summarized in Table 1 below for comparison.

TABLE 1

| Example | Alpha value | Surface Area Total (micro + meso) | Hexane Sorption (mg/g) |
|---|---|---|---|
| 3A | 22 | 430 (308 + 122) | 97 |
| 3B (0.75 wt % P) | 120 | 406 (209 + 197) | 94 |
| 3C (1.5 wt % P) | 110 | 495 (213 + 201) | 92 |
| Calcined 2A | 930 | 495 (418 + 77) | 105 |
| 4A | 18 (2%) | 416 (297 + 119) | 97 |
| Calcined 2B | 490 | 456 (386 + 67) | 96 |
| 4B | 100 (20.4%) | 441 (264 + 178) | 96 |
| Calcined 2C | 270 | 323 (276 + 47) | 92 |
| 4C | 71 (26.3%) | 423 (221 + 202) | 91 |

The results in Table 1 show that the P-treated catalyst (with and without calcination) produced by the present process maintained relatively high alpha values of ≥100 (as compared to <25 for the non P-treated catalyst) after severe steam treatment at ~1000° F. (~540° C.) and ~1 atmosphere (~100 kPa) steam for about 48 hours.

Example 5: 0.75 wt % P-Containing ZSM-5 Crystals Bound with Alumina

About 65 parts by weight (basis: calcined ~538° C.) of Example 2B crystal were mixed with about 35 parts by weight of Versal™ 300 pseudoboehmite alumina (basis: calcined ~538° C.) in a muller. Sufficient water was added to produce an extrudable paste on a ~2" Bonnot™ extruder. The mix of P-ZSM-5 crystals, pseudoboehmite alumina, and water containing paste was extruded and dried in a hotpack oven at ~121° C. overnight (~8-16 hours). The dried extrudate containing $P_2O_5$ was calcined in air at ~538° C. to convert the ZSM-5 to the H-form. The alpha value of the resulting catalyst was about 360.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing a phosphorus-modified zeolite catalyst, said process comprising:
   (a) heating an aqueous reaction mixture comprising a source of silica and a source of an organic directing agent effective to direct a synthesis of a ZSM-5 zeolite from said aqueous mixture, said heating being conducted at a temperature and for a time sufficient to produce crystals of the ZSM-5 zeolite;
   (b) separating wet zeolite crystals from the aqueous mixture produced in (a);
   (c) without removing all the water from the wet zeolite crystals to provide crystals having an Adsorption Factor from about 0.1 to less than 1.5, effecting the steps of:
      (i) converting the wet zeolite crystals into an ammonium form by ion exchange; and
      (ii) treating the ammonium form of the wet zeolite crystals with a phosphorus compound to produce a phosphorus-treated, ammonium-exchanged zeolite;
   (d) forming the phosphorus-treated, ammonium-exchanged zeolite from (c) into a catalyst; and
   (e) heating the catalyst in one or more stages to remove the water and organic directing agent from the zeolite crystals and to convert the zeolite crystals from the ammonium form to a hydrogen form.

2. The process of claim 1, wherein said reaction mixture also comprises a source of alumina.

3. The process of claim 2, wherein a molar ratio of silica to alumina in the reaction mixture is from about 20 to about 500.

4. The process of claim 2, wherein a molar ratio of silica to alumina in the reaction mixture is from about 20 to about 150.

5. The process of claim 1, wherein the zeolite crystals have an average crystal size of about 0.05 microns or less.

6. The process of claim 1, wherein said organic directing agent comprises n-propylamine.

7. The process of claim 1, wherein said temperature is from about 100° C. to about 200° C. and said time is from about 12 hours to about 120 hours.

8. The process of claim 1, wherein the separating (b) is accomplished by filtration.

9. The process of claim 1, wherein said wet zeolite crystals employed in (c) have an Adsorption Factor from about 0.2 to about 0.8.

10. The process of claim 1, wherein the converting (c) (i) and the treating (c) (ii) are accomplished simultaneously.

11. The process of claim 1, wherein the treating (c) (ii) is accomplished by impregnation.

12. The process of claim 1, wherein the treating (c) (ii) is accomplished by impregnating the zeolite crystals with an aqueous solution of an ammonium salt of a phosphorus oxyacid.

13. The process of claim 1, wherein the forming (d) comprises mixing the phosphorus-treated, ammonium-exchanged zeolite with a binder to form an extrudable composition and then extruding said composition to form the catalyst.

14. The process of claim 1, wherein the heating to remove the organic directing agent from the zeolite crystals and to convert the zeolite to the hydrogen form is accomplished in a single heating step.

15. The process of claim 14, wherein said single heating step is conducted at a temperature from about 500° C. to about 600° C. for a time from about 2 hours to about 12 hours.

* * * * *